United States Patent [19]

Merianos et al.

[11] 3,976,587
[45] Aug. 24, 1976

[54] AMINO DERIVATIVES OF TETRASUBSTITUTED BENZENE COMPOUNDS

[75] Inventors: John J. Merianos, Jersey City; Phillip Adams, Murray Hill, both of N.J.

[73] Assignee: Millmaster Onyx Corporation, New York, N.Y.

[22] Filed: June 10, 1975

[21] Appl. No.: 585,657

Related U.S. Application Data

[60] Continuation-in-part of Ser. No. 549,170, Feb. 12, 1975, Pat. No. 3,960,538, which is a division of Ser. No. 360,448, May 15, 1974, Pat. No. 3,886,284, which is a continuation-in-part of Ser. No. 291,824, Sept. 25, 1972, Pat. No. 3,838,197, which is a continuation-in-part of Ser. No. 130,783, April 2, 1971, Pat. No. 3,821,407.

[52] U.S. Cl. .................. 252/106; 134/42; 252/107; 260/570.5 R; 260/570.5 P; 424/330

[51] Int. Cl.² .................. C11D 3/46; C07C 87/20

[58] Field of Search ............ 252/106, 107; 424/330; 134/42; 260/570.5 P, 570.5 R

[56] References Cited

UNITED STATES PATENTS

| | | | |
|---|---|---|---|
| 3,645,715 | 2/1972 | Daum et al. | 71/67 |
| 3,663,620 | 5/1972 | Merianos et al. | 260/570.5 P |
| 3,717,579 | 2/1973 | Hofmann et al. | 252/106 |
| 3,733,421 | 5/1973 | Merianos et al. | 424/330 |

FOREIGN PATENTS OR APPLICATIONS

1,939,921   4/1970   Germany

*Primary Examiner*—P.E. Willis, Jr.
*Attorney, Agent, or Firm*—Arthur A. Jacobs

[57] ABSTRACT

The compound N-trimethylbenzyl diethylenetriamine and its use in a disinfectant and cleansing composition containing a surfactant selected from the group consisting of anionic, cationic and non-ionic surfactants.

7 Claims, No Drawings

AMINO DERIVATIVES OF TETRASUBSTITUTED BENZENE COMPOUNDS

This is a continuation-in-part of co-pending application Ser. No. 549,170, filed Feb. 12, 1975, now U.S. Pat. No. 3,960,538, which is, in turn, a division of application Ser. No. 360,448, filed May 15, 1974 and issued as U.S. Pat. No. 3,886,284 on May 27, 1975, the latter being a continuation-in-part of application Ser. No. 291,824, filed Sept. 25, 1972, now U.S. Pat. No. 3,838,197, which was a continuation-in-part of application Ser. No. 130,783, filed Apr. 2, 1971 and issued as U.S. Pat. No. 3,821,407 on June 28, 1974.

This invention relates to a new and novel disinfectant which is effective in the disinfection of hard surfaces such as hospital floors, walls, manufacturing equipment etc., and is, at the same time, compatible with anionic, cationic and non-ionic surfactants and detergents, so that it can be used together with them in a single formulation.

In accordance with the present invention, it has been discovered that N-trimethylbenzyl diethylenetriamine is a potent hard surface disinfectant and is compatible with anionic, cationic and non-ionic surfactants and detergents. It is, therefore, possible to include both N-trimethylbenzyl diethylenetriamine and any kind of detergent in one formulation which can be used both to disinfect and cleanse hard surfaces simultaneously.

In addition, it is possible to emulsify or disperse N-trimethylbenzyl diethylenetriamine in aqueous solution with either anionic, cationic or non-ionic surfactants. This gives the formulation of commercially available disinfectants a considerable amount of flexibility, so that other additives may be incorporated without being limited by the nature of the surfactant.

The best known commercially important organic disinfectants may be divided into three main groups for convenience, namely; quaternary ammonium salts, phenolic derivatives, and pine oil.

The quaternary ammoniuim salts, being cationic in nature, are incompatible with anionic surfactants and detergents.

Phenolic compounds are known to lose their ability to disinfect when they are in the presence of non-ionic surfactants or detergents; and often lose all of their disinfection activity within a matter of hours.

Pine oil, although itself compatible with all three classes of surfactants and detergents, has such a low order of effectiveness that it must be fortified with auxiliary disinfecting agents in order to make the formulation effective at reasonable concentrations in aqueous solution. Since the auxiliary disinfecting agents come from the classes quaternary ammonium salts and phenolic compounds, these fortifying materials limit the choice of emulsifier or detergent which may be included in the formulation.

N-trimethylbenzyl diethylenetriamine, on the other hand, is neither a quaternary ammonium salt, nor a phenol, and it is compatible with all classes of surfactants.

Another important aspect of the present invention is that since N-trimethylbenzyl diethylenetriamine is an amine base, it acts to form ammonium salts with acidic organic compounds such as fatty acids, alkylbenzene hydrogen sulfonates, alkyl hydrogen sulfates, alkyl hydrogen sulfonates, alkyl polyether hydrogen sulfates, mono-and di-alkyl hydrogen phosphates, alkyl aryl hydrogen phosphates, and the like. It also acts to form ammonium salts with mineral acids.

The aforementioned salts are capable of retaining the disinfectant properties of the free amine as well as the detergent and/or dispersive properties of the amine mixed with a detergent or surfactant.

EXAMPLE 1

The Preparation of 2,4,5-Trimethylbenzyl Chloride

Pseudocumene was chloromethylated by the procedure described by R. D. Lake and B. B. Corson, in the Journal of Organic Chemistry, Volume 24, pp. 1823–4. After purification by distillation, 2,4,5-trimethylbenzyl chloride was obtained in a yield that was about 80% of theoretical.

EXAMPLE 2

The Preparation of N-2,4,5-Trimethylbenzyl Diethylenetriamine:

515 grams of diethylenetriamine (about 5.0 moles) was placed in a round-bottom flask fitted with a stirrer, reflux condenser and dropping funnel. The dropping funnel was charged with 169 grams of purified trimethylbenzyl chloride from example 1 (about 1.0 moles), and the chloride was added slowly to the amine. The temperature was maintained at about reflux temperature with constant stirring. The addition took about 30 minutes. Then the adduct was cooled. Analysis for ionic chloride showed that the reaction was about 100% complete.

Then about 200 ml. of 30% aqueous caustic was added, with stirring, to liberate the product from its hydrochloride salt, and the free amine was extracted with about 1 liter of chloroform in a separatory funnel.

After stripping the chloroform, the pure amine product was obtained in about 95% of theoretical yield by distillation at 180°–190°C at 5 mm.

The undistilled amine was found to be suitable for commercial purposes, after stripping off the chloroform.

The hydrochloride of the pure amine melted at 195°–200°C.

N-trimethylbenzyl diethylenetriamine, together with inactive surfactants, was tested for microbiocidal activity against *P. aeruginosa* using the "Use Dilution Test" as described in "Official Methods Of Analysis Of The Association Of Official Analytical Chemists", 11th edition, 1970, page 61, published by the Association Of Official Analytical Chemists, Washington, D.C.

The passing criteria was at least 59 negative subcultures in 60 replicates at the indicated concentration in ppm of the tested compound. After establishing a lower concentration, some samples were tested at a higher concentration using 30 replicates.

The following tables are based on the number of negative subcultures over the number of replicate steel cylinders inoculated with *P. aeruginosa* and exposed to various dilutions of the experimental compound for 10 minutes prior to subculture in Letheen broth. In these tables N-2,4,5-trimethylbenzyl diethylenetriamine is "Compound A", "Permakleer 100" is tetrasodium salt of ethylenediamine tetracetic acid, 40% aqueous solution, "N 656" is nonyl phenyl polyethyleneoxide (11 moles), and "Maprofix WAC" is sodium lauryl sulfate, 30% aqueous solution. Permakleer 100, N 656, and Maprofix WAC are manufactured by the Onyx Chemical Company, Jersey City, New Jersey. "Deriphat 151"

is sodium N-coco-β-aminopropionate, an anionic surfactant manufactured by General Mills Chemicals, Minneapolis, Minn.; "Ammonyx LO" is lauryl-dimethylamine oxide, an amine oxide manufactured by Onyx Chemical Company, Jersey City, N.J.; "Groco Fatty Acids" coconut fatty acids, manufactured by A. Gross and Co., Div. Millmaster Onyx, Newark, N.J.; "Conoco C-560 (60%)" is sodium dodecylbenzene sulfonate, an anionic surfactant manufactured by Continental Oil Co., Parker City, Nebraska; "TKPP" is tetrapotassium pyrophosphate.

Table 1

| Formulation | I(Parts by Wt.) | II(Parts by Wt.) |
|---|---|---|
| Compound A | 4.5 | 4.5 |
| Na$_2$CO$_3$ | 3.0 | 3.0 |
| "Permakleer 100" | 2.5 | 2.5 |
| "N 656" | 4.5 | |
| "Maprofix WAC" | | 10.0 |
| Water | 85.5 | 80.0 |
| Formulation | III(Parts by Wt.) | IV(Parts by Wt.) |
| Compound A | 4.5 | 4.5 |
| Na$_2$CO$_3$ | 3.0 | 3.0 |
| "Permakleer 100" | 2.5 | 2.5 |
| Deriphat 151 | 4.5 | |
| Ammonyx LO | | 15.0 |
| Water | 85.5 | 75.0 |
| Formulation | V(Parts by Wt.) | VI(Parts by Wt.) |
| Compound A | 4.5 | 4.5 |
| TKPP | 8.5 | 6.0 |
| NaOH | | 1.7 |
| Conoco-C 560 (60%) | 25.0 | |
| Groco Fatty Acid | | 9.0 |
| Isopropanol | 10.0 | 10.0 |
| Water | 52.0 | 68.8 |

Table 2

| | Negative Subcultures At Indicated Concentrations | | | | | |
|---|---|---|---|---|---|---|
| | I | II | III | IV | V | VI |
| 1oz/gallon equivalent to 350 ppm of Compound A | | | 56/60 | 57/60 27/30 | 44/60 20/30 | 55/60 28/30 |
| 2oz/gallon equivalent to 700 ppm of Compound A | 50/60 | 60/60 | 60/60 60/60 | 60/60 60/60 | 60/60 60/60 | 60/60 60/60 |
| 3oz/gallon equivalent to 1050 ppm of Compound A | 60/60 | | 60/60 | 50/50 | 60/60 | 60/60 |
| 4oz/gallon equivalent to 1400 ppm of Compound A | 30/30 | | 30/30 | 20/20 | 20/20 | 30/30 |

The results of the Use Dilution Test show that the compound of this invention is an effective disinfectant at concentrations about 1050 ppm when used together with non-ionic surfactants, and at concentrations of about 700 ppm when used together with anionic surfactants, and at concentrations of about 700 ppm when used together with amine oxide surfactants. These minimum effective values are only slightly higher than the best quaternary ammonium salts used alone, for disinfection, but unlike the quaternary ammonium salts, the compound of the present invention can be used effectively with anionic surfactants or detergents.

Insofar as concerns any maximum concentrations, they do not actually come into consideration because any concentration above the minimums noted above would be effective for the purpose, and any increase in concentration would serve little purpose.

It is to be understood that the surfactants used in these tests are merely exemplifications of such surfactants generally, any of which can be used for the same purpose. In this respect, the following types of surfactants are illustrative of those which may be utilized:

Anionic surfactants: alkyl sulfate salts, alkyl polyethyleneoxy sulfate salts, alkyl phenol polyethyleneoxy sulfate salts, alkylbenzene sulfonate salts, olefin sulfonate salts, β-acylamido propionate salts, sarcosinates, taurates, and fatty acid salts.

Non-ionic surfactants: alkyl polyethyleneoxy ethers, alkyl phenol polyethyleneoxy ethers, polyethyleneoxy amines, polyethyleneoxy fatty acids, alkyl dimethyl amino oxides, and the "Pluronics" (BASF — Wyandotte, Mich.)

Cationic surfactants: alkyltrimethyl ammonium halides, dialkyldimethyl ammonium halides, alkylbenzyl dimethyl ammonium halides, and imidazolinium salts, pyridinium salts, and quinolinium salts.

Specific surfactants utilizable in this invention are, inter alia, those disclosed, for example in, "Surface Active Agents and Detergents", Schwartz, Perry & Berch, Interscience Publishers, Inc., New York, 1958, Vol. I, 1949–1963, Vol. II 1958.

The minimum effective concentration of phenol surfactants is of the same order of magnitude as quaternary salts; but, unlike the compound of our invention, phenol disinfectants cannot be used together with non-ionic surfactants or detergents.

The invention claimed is:

1. The compound N-trimethylbenzyl diethylenetriamine.

2. A method of simultaneously disinfecting and cleansing a surface which comprises applying to said surface an effective amount sufficient to disinfect and cleanse said surface of a mixture of N-trimethylbenzyl diethylenetriamine and a surfactant selected from the group consisting of anionic, cationic and non-ionic surfactants.

3. The method of claim 2 wherein said N-trimethylbenzyl diethylenetriamine is used in a concentration of at least about 1050 ppm relative to the total composition and wherein the surfactant is an non-ionic surfactant.

4. The method of claim 2 wherein said N-trimethylbenzyl diethylenetriamine is used in a concentration of at least about 700 ppm relative to the total composition and wherein the surfactant is an anionic surfactant.

5. A disinfectant and cleansing composition consisting essentially of a mixture of a disinfectant consisting of N-trimethylbenzyl diethylenetriamine and a surfactant selected from the group consisting of anionic, cationic and non-ionic surfactants, the disinfectant and the surfactant each being present in an effective amount for its purpose.

6. The composition of claim 5 wherein said N-trimethylbenzyl diethylenetriamine is used in a concentration of at least about 1050 ppm relative to the total composition and wherein the surfactant is an non-ionic surfactant.

7. The composition of claim 5 wherein said N-trimethylbenzyl diethylenetriamine is used in a concentration of at least about 700 ppm relative to the total composition and wherein the surfactant is a anionic surfactant.

* * * * *